(12) United States Patent
Stinson (10) Patent No.: US 10,993,481 B2
(45) Date of Patent: May 4, 2021

(54) ONE-PIECE GARMENT

(71) Applicant: Siiri Stinson, Wilton, ME (US)

(72) Inventor: Siiri Stinson, Wilton, ME (US)

( * ) Notice: Subject to any disclaimer, the term of this patent is extended or adjusted under 35 U.S.C. 154(b) by 61 days.

(21) Appl. No.: 15/895,891

(22) Filed: Feb. 13, 2018

(65) Prior Publication Data

US 2019/0246707 A1 Aug. 15, 2019

(51) Int. Cl.
*A41B 13/00* (2006.01)
*A41D 11/00* (2006.01)
*A41D 13/12* (2006.01)

(52) U.S. Cl.
CPC ............ *A41B 13/005* (2013.01); *A41D 11/00* (2013.01); *A41D 13/1263* (2013.01)

(58) Field of Classification Search
CPC .. A41B 13/005; A41D 11/00; A41D 13/1263; A41D 13/12; A41D 13/04; A41D 10/00; A41D 1/04; A41D 1/18; A41D 13/1272; A41D 13/1245; A41D 13/0568; A41D 13/0005; A41D 13/0007; A41D 3/08; A41D 13/046; A41D 13/129; A41D 27/10; A41D 27/22; A41D 3/00; A61F 5/37
USPC ......... 2/69, 114; 128/869; 24/298, 301, 302, 24/304
See application file for complete search history.

(56) References Cited

U.S. PATENT DOCUMENTS

| | | | | | |
|---|---|---|---|---|---|
| 1,999,010 | A * | 4/1935 | Tait | ........................... | A41D 7/00 450/30 |
| 2,162,948 | A * | 6/1939 | Gosselin | ................ | A41D 11/00 2/111 |
| 2,616,085 | A * | 11/1952 | Bottolfsen | ............. | A41D 13/04 2/69 |
| 3,901,229 | A * | 8/1975 | Hensel | ................... | A61F 5/3784 128/873 |
| 4,257,127 | A * | 3/1981 | Kaupin | ................ | A41B 13/005 2/75 |
| 4,304,006 | A * | 12/1981 | Swart | ................... | A41B 13/005 2/49.1 |
| 5,494,052 | A * | 2/1996 | Grohman | ............... | A61F 5/3769 128/873 |
| 6,817,031 | B1 * | 11/2004 | Gravlin | .................... | A41D 1/00 2/67 |
| 7,810,172 | B2 * | 10/2010 | Williams | ........... | A41D 13/1272 2/114 |
| 8,490,212 | B1 * | 7/2013 | Asher | ....................... | A41D 1/04 2/2.5 |
| 10,064,440 | B2 * | 9/2018 | Levine | ............... | A41D 13/1236 |
| 2002/0121247 | A1 * | 9/2002 | Sharpe | ................... | A61H 39/04 119/820 |
| 2008/0120819 | A1 * | 5/2008 | Rene | ......................... | F41H 1/02 24/68 R |
| 2008/0295210 | A1 * | 12/2008 | Matic | ........................ | F41H 1/02 2/2.5 |

(Continued)

FOREIGN PATENT DOCUMENTS

FR 805629 A * 11/1936 ............... A41D 7/00

*Primary Examiner* — Khoa D Huynh
*Assistant Examiner* — Uyen T Nguyen
(74) *Attorney, Agent, or Firm* — Foley & Lardner LLP (57) ABSTRACT

The disclosure relates to a one-piece garment that fastens securely and snugly in the neck and back through a unique threading system, has static arm holes snug enough to prevent diaper access, gives room through inner leg paneling for a pull-up, and has tapering legs with static openings to prevent diaper access through modification of the leg.

15 Claims, 11 Drawing Sheets

(56) References Cited

U.S. PATENT DOCUMENTS

| | | | |
|---|---|---|---|
| 2009/0144876 A1* | 6/2009 | Pena | A41D 13/0007 2/102 |
| 2010/0017933 A1* | 1/2010 | Taylor-Barry | A41D 13/1254 2/83 |
| 2012/0042439 A1* | 2/2012 | Dyster | A45F 5/02 2/311 |
| 2017/0273365 A1* | 9/2017 | Muhlenfeld | A41C 3/12 |
| 2017/0332711 A1* | 11/2017 | Rabin | A41D 13/1263 |

* cited by examiner

ONE-PIECE GARMENT

BACKGROUND

Scatolia, more commonly known as fecal smearing, is a common problem in children and adults with various genetic and clinical diagnoses (e.g. Autism, Angelman Syndrome, Dementia, Alzheimer's), as well as children who are going through a normal phase of child development. These individuals have the ability to undress and remove pull-ups but lack the cognitive understanding to choose a proper time and place to do so or have sensory or behavioral issues that prompt fecal smearing. Regardless of the cause, dealing with scatolia is difficult and time consuming. Indiscriminate nudity, especially when combined with the wandering tendencies associated with these populations, presents an additional problem. Safety, sanity, and hygiene can be at stake. Parents and caregivers who regularly clean up after fecal smearing incidents spend hours cleaning and disinfecting. In addition to the physical labor required for such efforts, parents and caregivers also experience a drain on the emotional resources needed to give the needed level of care long term due to the heightened stress level caused by the indiscriminate nudity, and incontinence combined with fecal smearing. Individuals who gain access to fecal matter in this way and ingest it are also at increased risk for contraction of Hepatitis A and Hepatitis B.

For individuals with dexterity and persistence, current market offerings attempting to help with this problem are insufficient. Current offerings have a static neck, but the fastening system is elementary and can be overcome easily, sometimes with one hand. In addition, the arm holes are loose enough to allow access to diaper or pull-up through retracting arms through the arm holes and into the body of the garment. Some have a secure fastening system but are short enough or loose enough for the wearer to gain access to a pull-up or diaper through the leg of the garment. Some are also made with weak seam structure or fabric construction which allows for tearing the garment and rendering it useless.

SUMMARY

Aspects of the present disclosure relate generally to a one-piece garment that fastens securely and snugly in the neck and back through a unique threading system, has static arm holes snug enough to prevent diaper access, gives room through inner leg paneling for a pull-up, and has tapering legs with static openings to prevent diaper access through modification of the leg.

One implementation disclosed herein is a garment including two front panels, two back panels, and an inner leg panel. The two front panels are coupled together to form a front portion of the garment and the two front panels form a high rounded neck edge. The two back panels are coupled together to form a back portion of the garment. The front portion and the back portion of the garment are coupled together and include a neck hole edge covered with a folded ribbon configured to provide a passageway at the neck hole edge for a drawstring around the neck hole edge. The front portion and the back portion of the garment include two arm hole sections. The drawstring around the neck hole edge exits the passageway at two holes in the folded ribbon at the back portion of the garment. The inner leg panel is coupled to a lower edge of the front portion and the back portion. The front portion, back portion, and inner leg panel are fitted together using an interlocking seam. The two back panels include two loops of ribbon at the two arm hole sections and a strip of looping ribbon across the two back panels. The drawstring exits the passageway, crosses itself, passes through the two loops of ribbon and is configured to be tied off at the strip of looping ribbon.

Another implementation disclosed herein is a garment including a front panel, a back panel, and an inner leg panel. The front panel forms a front portion of the garment and forms a high rounded neck edge. The back panel forms a back portion of the garment. The front portion and the back portion of the garment are coupled together and include a neck hole edge having a passageway for a drawstring. The front portion and the back portion of the garment include two arm hole sections. The drawstring around the neck hole edge exits the passageway at two holes at the back portion of the garment. The inner leg panel is coupled to a lower edge of the front portion and the back portion. The front portion, back portion, and inner leg panel are fitted together using an interlocking seam. The back panel includes two loops of ribbon at the two arm hole sections and a strip of looping ribbon across the back panel. The drawstring exits the passageway, crosses itself, passes through the two loops of ribbon and is configured to be tied off at the strip of looping ribbon.

In some implementations, the two back panels of the garment are coupled together using a seam half-way up the back portion of the garment, leaving a vertical gap from a center of the neck hole edge to a middle of the back portion of the garment. In other implementations, the strip of looping ribbon includes intermittent stitching to connect the strip of looping ribbon to the two back panels. The garment can also include sleeves coupled to the front portion and the back portion at the arm hole sections. The strip of looping ribbon can be located above a mid-way point of the back portion of the garment. The strip of looping ribbon can be located below a mid-way point of the back portion of the garment. The inner leg panel includes tapering leg portions with static openings. The inner leg panel can be configured to permit wearer of the garment to wear a diaper. The inner leg panel can be configured to be one cut double a length of an inseam of an individual.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

Illustrative embodiments will hereafter be described with reference to the accompanying drawings.

FIGS. 1-1, 1-2, 1-3, and 1-4 show an illustrative method of interlocking seams found on the front, side, low back and inseam of a garment according to particular embodiments.

FIGS. 2-1, 2-2, and 2-3 illustrate a double folded seam process found on the neck, upper back, armhole and leg hole of the garment of FIG. 1 according to particular embodiments.

FIGS. 3-1, 3-2, and 3-3 present an illustrative method of incorporating a length of ribbon into the folded seam on the upper back and armhole of the garment of FIG. 1 according to particular embodiments.

FIGS. 4-1 and 4-2 show the static cuff process of covering the folded seam with ribbon found at the armhole and leg hole of the garment of FIG. 1 according to particular embodiments.

FIGS. 5-1 and 5-2 illustrates the incorporation of a drawstring to the ribbon-covered seam found at the neck of the garment of FIG. 1 according to particular embodiments.

FIGS. 8-1 and 8-2 illustrate two front panels and an example inner leg panel that form a front portion of the garment of FIG. 1, according to particular embodiments.

FIGS. 11-1, 11-2, and 11-3 illustrate an inner leg panel coupled to a lower edge of the front portion and the back portion of the garment of FIG. 1, according to particular embodiments.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

According to an illustrative embodiment, a garment is made from five cuts of fabric: two front, two back, and one inner leg panel. The illustrative garment also uses a length of parachute cord or lacing, a length each of 1" and 1½" wide fabric ribbons, and thread. Fabrics used can include fleece, 95% cotton/5% spandex, and 100% cotton. It may also be manufactured using cotton fabric interwoven with silver. Fleece requires single layer fabric, while the cotton/spandex and 100% cotton fabrics require double fabric layering of each cut. The front cuts of fabric allow for a high rounded neck with dimensions following the dimensions of the intended wearer (regular sizing for typically sized individuals, larger or smaller as needed where needed, keeping in mind the garment must not be too roomy), including inch seam allowances. The back cuts of fabric come to the base of the neck and follows the dimensions of the intended wearer with an inch seam allowance. The back cuts are seamed together in the center only halfway up, leaving a vertical gap from the center of the neckline down to the middle of the back (length varies depending on size of garment) where each side is individually seamed. The inner leg panel is one cut double the length of the individual's inseam with an inch seam allowance on each end.

Each front, side, and lower back seam, as well as the inseam, is carefully fitted together in an interlocking fashion. FIGS. 1-1, 1-2, 1-3, and 1-4 illustrate an example process of forming interlocking seams found on the front, side, low back and inseam of a garment. This process includes [1] folding an inch seam allowance of the right side B of one cut under to form a half inch seam (FIG. 1-1), [2] folding the left side A of the opposing cut of fabric over to form a half inch seam (FIG. 1-2), and then [3] interlocking the two seams by sliding the cut edge side of each folded seam inside the other to form a seam without a ragged edge to minimize sensory issues for the individual (FIG. 1-3). Each seam is then [4] sewn with a double straight stitch, one on either side of the seam (FIG. 1-4).

The front panels are sewn together first, followed by the back panels only ⅓ of the way up, leaving the upper portion of the panels unconnected. The inner leg panel is incorporated next by attaching each edge to the inner leg of the front and back cuts of fabric with the same interlocking seam. Next, the outer leg side of the front and back panels are sewn together, followed by the shoulder seams.

FIGS. 2-1, 2-2, and 2-3 illustrate a double folded seam process found on the neck, upper back, armhole and leg hole of the garment. The leg hole seams are double folded [1] and [2] in preparation for coverage by the reinforcing ribbon (FIGS. 2-1 and 2-2). The leghole edge is folded under ½" once and then again, using the 1" seam allowance to create a folded under ½" seam. The armhole and upper back seams are also double folded. However, each incorporates a length of ribbon, inserted ½" into the seam during the second folding phase of seam preparation (FIG. 2-3).

FIGS. 3-1, 3-2, and 3-3 illustrate an example method of incorporating a length of ribbon into the folded seam on the upper back and armhole of the garment. FIG. 3-1 shows the ribbon folded into the first fold and FIG. 3-2 shows the ribbon folded into the second fold. On the armholes, the shorter length of ribbon is incorporated halfway down the back side of the armhole. On the upper back seams, the longer length of ribbon is incorporated ⅓ of the way down from the neck. Where each upper back side folded seam meets the interlocking lower back seam, the folded seam transitions to integrate with the interlocking seam (FIG. 3-3).

FIGS. 4-1 and 4-2 illustrate a static cuff process of covering the folded seam with ribbon found at the armhole and leg hole of the garment. The folded seam of the armhole is preferably covered by the 1" ribbon. FIG. 4-1 shows the ribbon is folded into two ½" halves. Into the inside crease, the finished folded seam slides, with the ends of the ribbon overlapping. Where the ends of the ribbon overlap, the upper segment folds under ¼" to hide the raw ribbon edge. The ribbon is double stitched to the folded seam, as shown in FIG. 4-2. This process is repeated on the other armhole and on each leghole.

FIGS. 5-1 and 5-2 illustrate incorporating a drawstring to the ribbon-covered seam found at the neck of the garment. The raw neck edge aligns with the length of drawstring so that the 1½" ribbon can fold over and cover it, as shown in FIG. 5-1. The ribbon folds in half with ¼" of each edge turned under, as shown in FIG. 5-2. The drawstring is placed adjacent to the neck edge, carefully avoiding perforation while the ribbon is double stitched to the neck.

Figure 1:
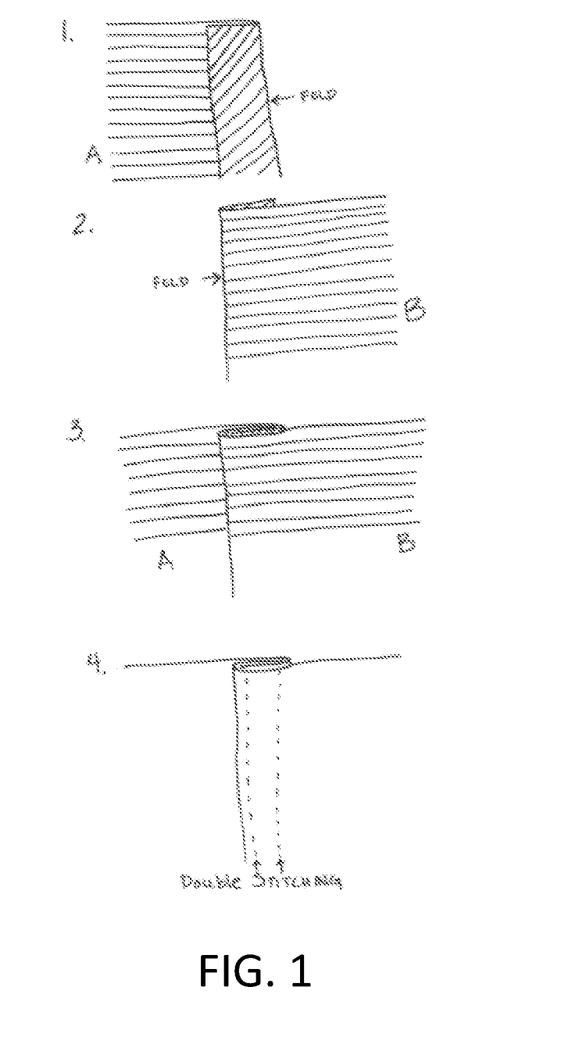
Figure 2:
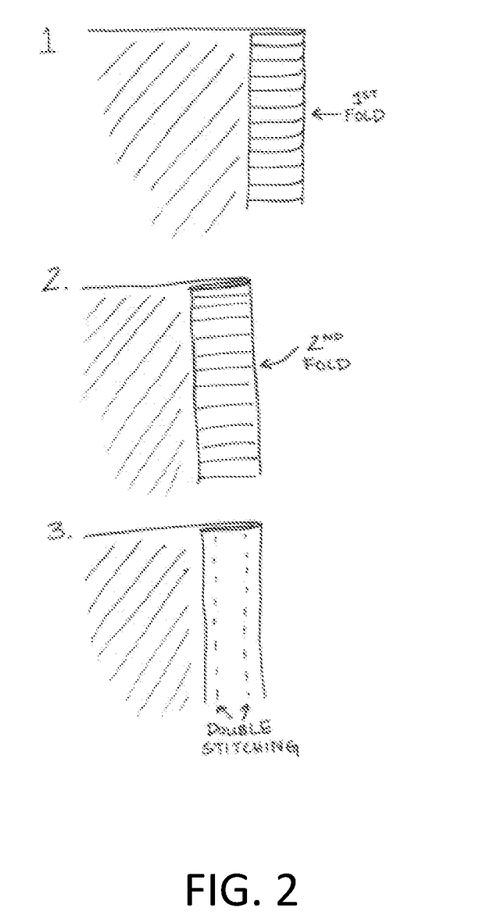
Figure 3:
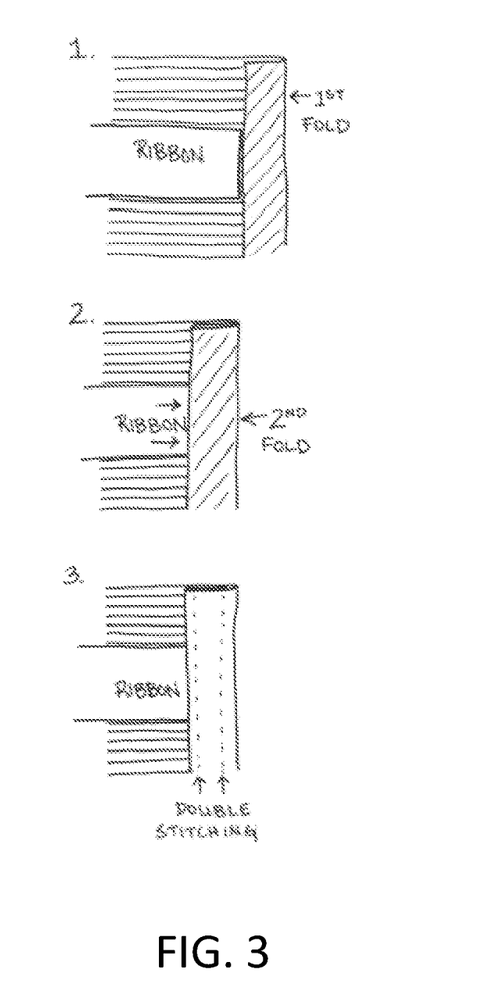
Figure 4:
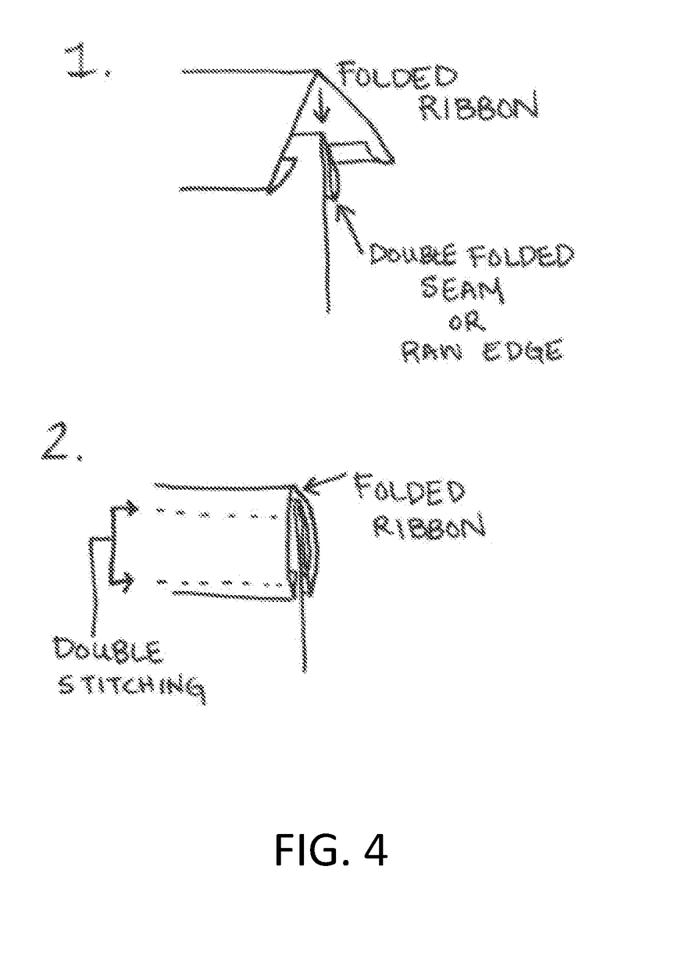
Figure 5:
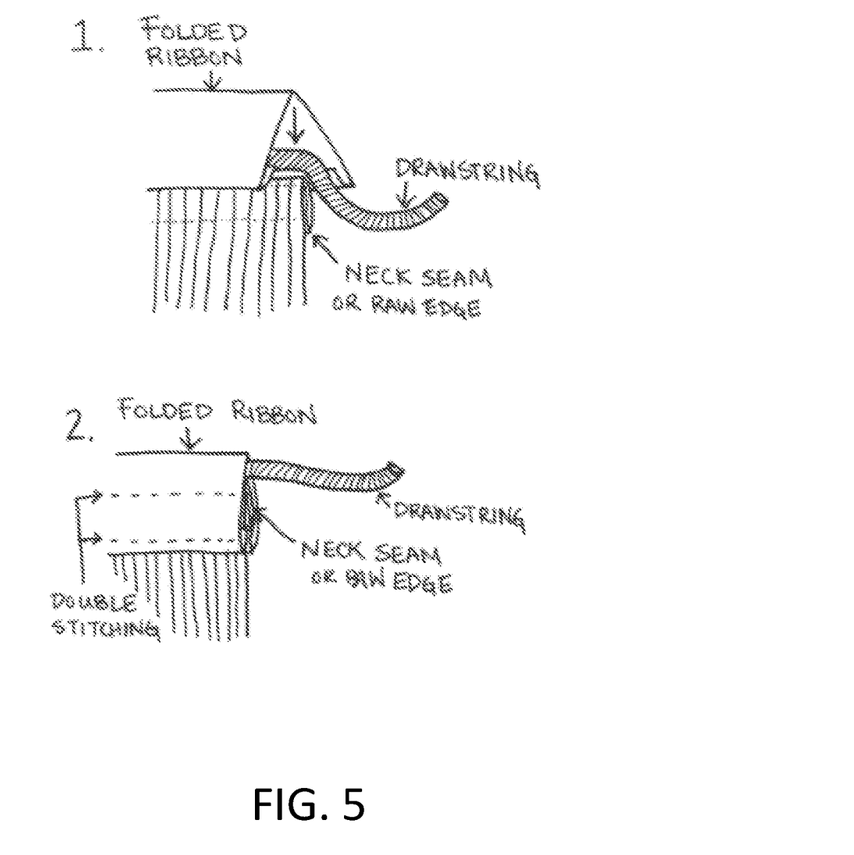
Figure 6:
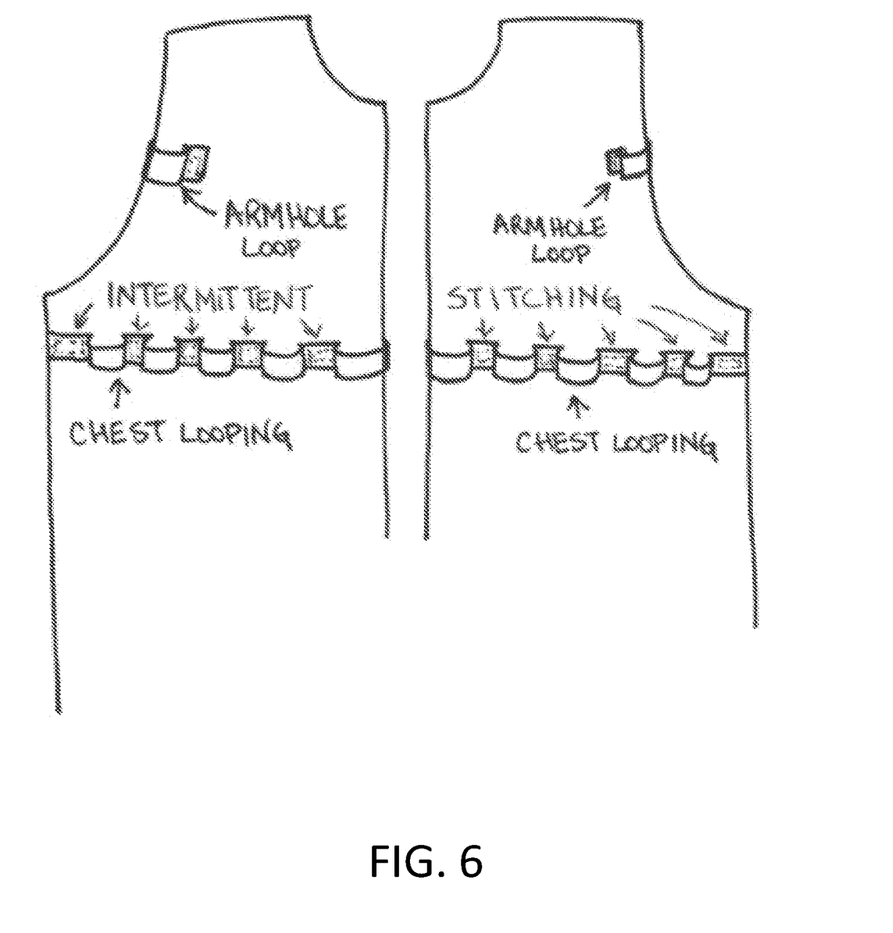
FIG. 6 shows the placement of the ribbon looping on the back and armholes of the garment of FIG. 1 to enable the adjustable threading system.

FIG. 6 shows placement of the ribbon looping on the back and armholes of the garment to enable an adjustable threading system. Five inches from the top of the right side of the back of the garment, another ribbon end is folded under ¼" and inserted on the inside of the seam perpendicular to the seam. The ribbon is then brought around the edge of the seam creating a small loose ½" loop of ribbon that is then secured by a triple ¾"×½" rectangular stitching pattern, without cutting the remaining length of ribbon. The ribbon is then secured every 1½" inches with a triple ¾"×1" square pattern of stitching, leaving a small 2" loop of loose ribbon between the stitching. After three such stitches, the last portion of the ribbon is secured at the side underarm seam using a triple ¾"×2" square stitching pattern. This process is repeated on the left side.

Figure 7:
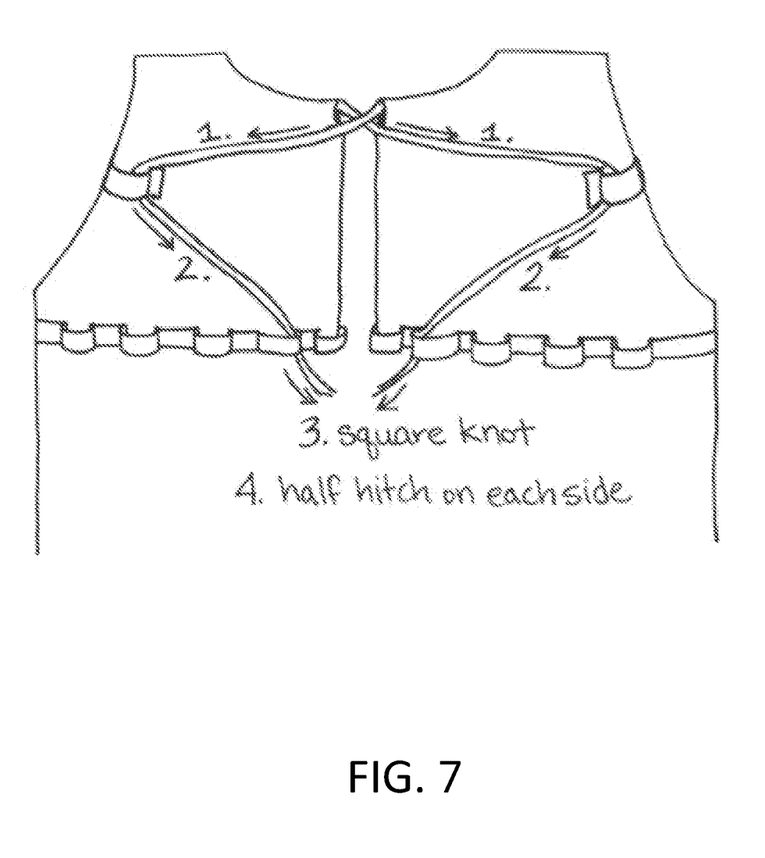
FIG. 7 presents an illustrative method of threading the looping system to adjust the garment to snugly fit the wearer according to particular embodiments.
Figure 8:
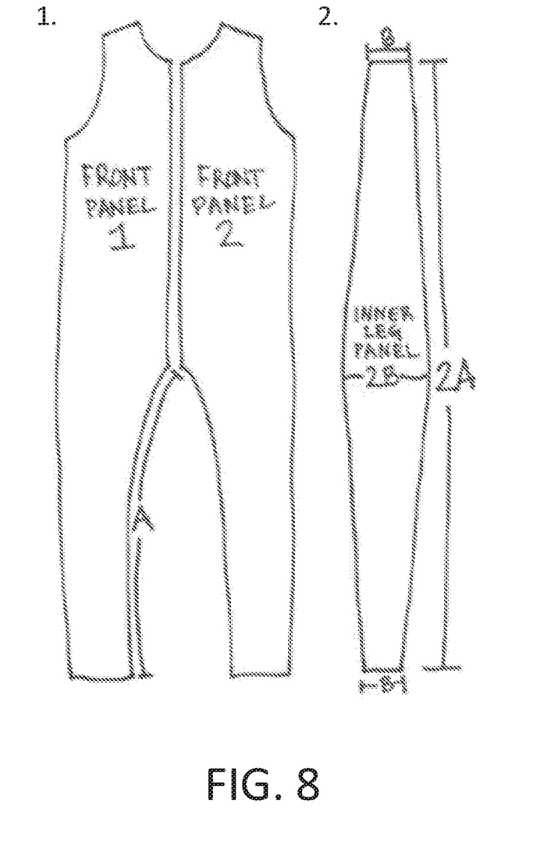

FIG. 7 illustrates threading the looping system to adjust the garment to snugly fit the wearer. In order to utilize the threading system, the cords from the neckline are crossed behind the shoulders and inserted into opposite loops on the back of each armhole. The cord can be crossed again or threaded straight down through one of the matching loops at either side of the vertical opening in the back of the garment.

The cords are pulled until the garment fits snugly and then tied together in a secure square knot, followed by a half hitch on each side. Last, the ends of the cords are tied into small double stopper knots to make sure they do not slip through the neck hole when the cord is untied, or the garment is washed.

The garment could also be made using an upper and lower front and back cut of fabric, secured by double stitching at the empire waist level to give variety to the outward appearance of the garment, while not sacrificing the security of the garment. The front top and bottom would be sewn together first, followed by the back top and bottom. Assembly would then proceed as outlined above. Sleeves could be added to the garment—either cap, short or long sleeves—and would be added at the step when the armholes are typically sewn. If sleeves are added, other than a cap sleeve, the garment assembly would be altered so that the ribbon on the armhole would be added along with the sleeve, with the ends of the ribbon incorporated with the sleeve seam. Alternatively, the garment could be altered to eliminate the ribbon at the neck by using a fabric that can be double layered and running the drawstring between the layers. To accommodate an adjustable armhole similar to the neckline, create a larger seam, similar to the original neck, allowing for threading a cord through the armhole. In this case, each end of the cord would be hand-sewn into a loop around a short length of ribbon, folded over and sewn to itself with triple stitching to create a loop of fabric. When added to the threading system, the cords would be crossed behind the shoulders and then passed through the loop at the armhole on the opposite side, securing the armhole.

Other fabric, lace or cord types could be used depending on the taste or sensory needs of the individual, as long as the material is strong enough to prevent tearing and flexible enough to allow for comfortable movement. Additional or alternative placement of the loops (e.g. higher, lower, fewer) could be used to tailor the garment to a particular individual's needs.

FIGS. 8-1 and 8-2 illustrate two front panels and an example inner leg panel that form a front portion of the garment of FIG. 1, according to particular embodiments.

Figure 9:
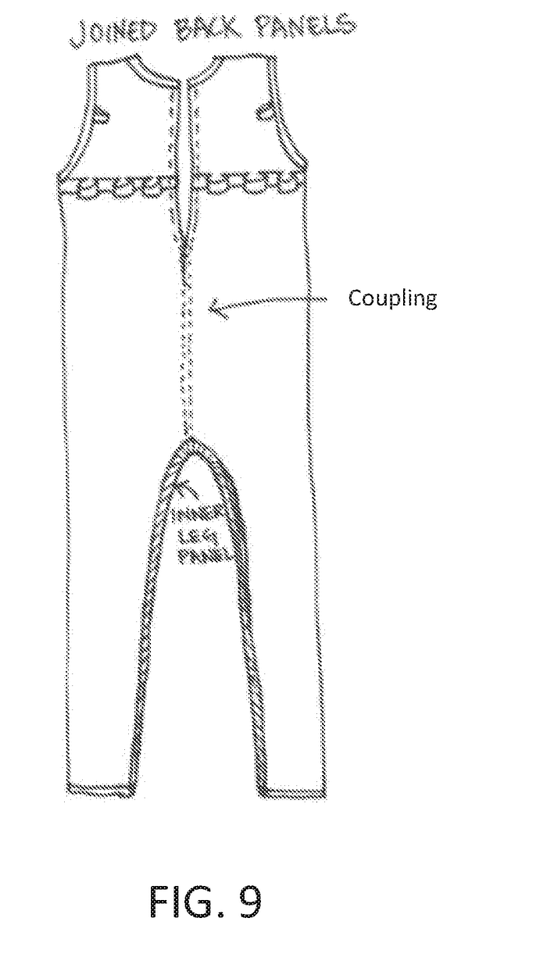
FIG. 9 illustrates two back panels coupled together using a seam half way up the back portion of the garment of FIG. 1, according to particular embodiments.

FIG. 9 illustrates two back panels coupled together using a seam half way up the back portion of the garment of FIG. 1, according to particular embodiments.

Figure 10:
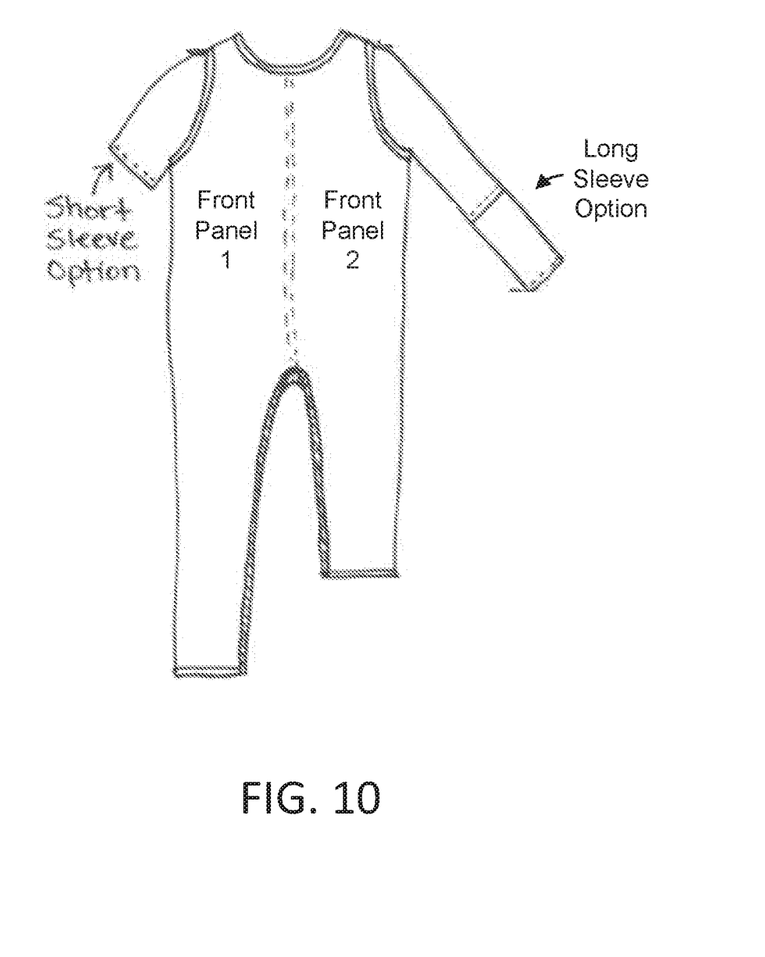
FIG. 10 illustrates two front panels coupled together to form a front portion of the garment of FIG. 1, according to particular embodiments.
Figure 11:
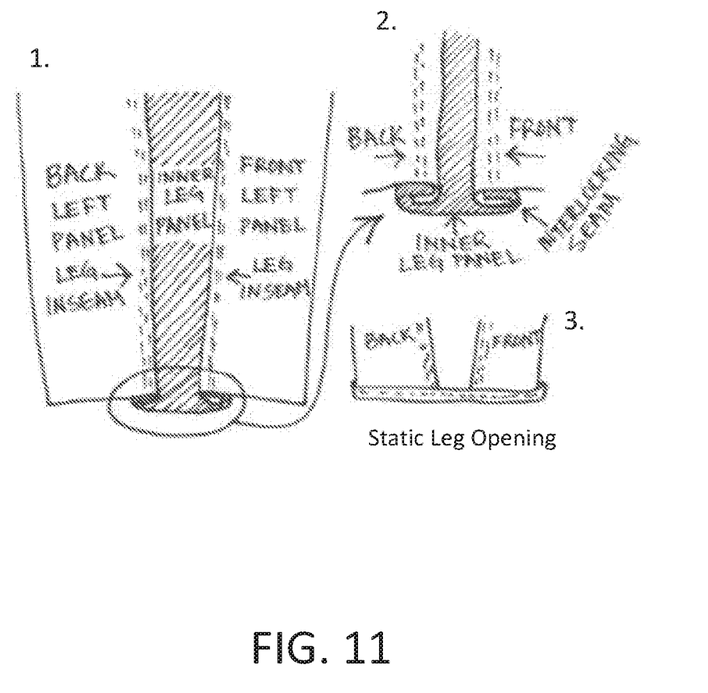

FIG. 10 illustrates two front panels coupled together to form a front portion of the garment of FIG. 1, according to particular embodiments.

FIGS. 11-1, 11-2, and 11-3 illustrate an inner leg panel coupled to a lower edge of the front portion and the back portion of the garment of FIG. 1, according to particular embodiments.

Advantageously, this garment prevents access to the diaper area of the wearer by the wearer. Moreover, the garment also prevents disrobing by the wearer.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A garment comprising:
    two front panels coupled together to form a front portion of the garment, wherein the two front panels form a rounded neck edge;
    two back panels coupled together to form a back portion of the garment, wherein the front portion and the back portion of the garment are coupled together and include a neck hole edge covered with a folded ribbon configured to provide a passageway at the neck hole edge for a drawstring around the neck hole edge, wherein the front portion and the back portion of the garment include two arm hole sections, wherein the drawstring around the neck hole edge exits the passageway at two holes in the folded ribbon at the back portion of the garment; and
    an inner leg panel coupled to a lower edge of the front portion and the back portion, wherein the front portion, back portion, and inner leg panel are fitted together using an interlocking seam,
    wherein the inner leg panel includes tapering leg portions,
    wherein the two back panels include two loops of ribbon at the two arm hole sections and two strips of looping ribbon across the two back panels, each strip of looping ribbon comprising a plurality of loops of ribbon,
    wherein the two strips of looping ribbon are in a substantially horizontal position parallel to the lower edge of the front portion and the back portion across the two back panels, each loop of ribbon of the plurality of loops of ribbon of each of the two strips of looping ribbon positioned horizontally next to each other in parallel with the lower edge of the front portion and the back portion and configured to receive the drawstring,
    wherein the two strips of looping ribbon each include intermittent stitching between each loop of ribbon of the plurality of loops of ribbon of the respective strips of looping ribbon to connect the strip of looping ribbon to one of the two back panels, wherein the intermittent stitching between each loop of ribbon of the respective strips of looping ribbon comprises square patterns of stitching every 1½ inches that form the loops of ribbon between the square patterns of stitching, each square pattern comprising a triple ¾ inch by 1 inch square pattern of stitching, wherein the drawstring exits the passageway, crosses itself, passes through the two loops of ribbon, passes through a loop of ribbon of the plurality of loops of ribbon of each of the two strips of looping ribbon, and is configured to be tied off below a side of the two strips of looping ribbon opposite the neck hole edge and over an outer face of the two back panels, as viewed in a direction perpendicular to the two back panels, and wherein the drawstring is configured to be pulled until the garment fits snugly and then tied off below the side of the two strips of looping ribbon in a square knot, followed by a half hitch on each side, and ends of the drawstring are tied into small double stopper knots.

2. The garment of claim 1, wherein the two back panels are coupled together using a seam half-way up the back portion of the garment, leaving a vertical gap from a center of the neck hole edge to a middle of the back portion of the garment.

3. The garment of claim 1, wherein the two strips of looping ribbon are located above a mid-way point of the back portion of the garment.

4. The garment of claim 1, wherein the two strips of looping ribbon are located below a mid-way point of the back portion of the garment.

5. The garment of claim 1, wherein the tapering leg portions include static openings.

6. The garment of claim 1, wherein a portion of each of the two strips of ribbon is secured at a side underarm seam of the garment using a triple ¾ inch by 2 inch square stitching pattern.

7. The garment of claim 1, wherein the inner leg panel is configured to be one cut double a length of an inseam of an individual.

8. A garment comprising:
a front panel forming a front portion of the garment, wherein the front panel forms a rounded neck edge;
a back panel forming a back portion of the garment, wherein the front portion and the back portion of the garment are coupled together and include a neck hole edge having a passageway for a drawstring, wherein the front portion and the back portion of the garment include two arm hole sections, wherein the drawstring around the neck hole edge exits the passageway at two holes at the back portion of the garment; and
an inner leg panel coupled to a lower edge of the front portion and the back portion, wherein the front portion, back portion, and inner leg panel are fitted together using an interlocking seam,
wherein the back panel includes two loops of ribbon at the two arm hole sections and two strips of looping ribbon across the back panel, each strip of looping ribbon comprising a plurality of loops of ribbon, wherein the inner leg panel includes tapering leg portions, wherein the two strips of looping ribbon each include intermittent stitching between each loop of ribbon of the plurality of loops of ribbon of the respective strip of looping ribbon to connect the strip of looping ribbon to the back panel, wherein the intermittent stitching between each loop of ribbon of the respective strips of looping ribbon comprises square patterns of stitching every 1½ inches that form the loops of ribbon between the square patterns of stitching, each square pattern comprising a triple ¾ inch by 1 inch square pattern of stitching, wherein the two strips of looping ribbon are each in a substantially horizontal position parallel to the lower edge of the front portion and the back portion across the back panel, each loop of ribbon of the plurality of loops of ribbon of each of the two strips of looping ribbon positioned horizontally next to each other in parallel with the lower edge of the front portion and the back portion and configured to receive the drawstring, and wherein the drawstring exits the passageway, crosses itself, passes through the two loops of ribbon, passes through a loop of ribbon of each of the plurality of loops of ribbon of each of the strips of looping ribbon, and is configured to be tied off below a side of the two strips of looping ribbon opposite the neck hole edge and over an outer face of the back panel, as viewed in a direction perpendicular to the back panel; and wherein the drawstring is configured to be pulled until the garment fits snugly and then tied off below the side of the two strips of looping ribbon in a square knot, followed by a half hitch on each side, and ends of the drawstring are tied into small double stopper knots.

9. The garment of claim 8, wherein the back panel includes a vertical gap from a center of the neck hole edge to a middle of the back portion of the garment.

10. The garment of claim 8, wherein the two strips of looping ribbon are located above a mid-way point of the back portion of the garment.

11. The garment of claim 8, wherein the two strips of looping ribbon are located below a mid-way point of the back portion of the garment.

12. The garment of claim 8, wherein the tapering leg portions include static openings.

13. The garment of claim 8, wherein the inner leg panel is configured to permit a wearer of the garment to wear a diaper.

14. The garment of claim 8, wherein the inner leg panel is configured to be one cut double a length of an inseam of an individual.

15. The garment of claim 1, wherein the drawstring is configured to be tied off over the outer face of the two back panels entirely below the two strips of looping ribbon.

* * * * *